United States Patent
Vilsmeier et al.

(10) Patent No.: US 7,324,626 B2
(45) Date of Patent: Jan. 29, 2008

(54) VOLUMETRIC IMAGING ON A RADIOTHERAPY APPARATUS

(75) Inventors: Stefan Vilsmeier, Kufstein (AT); Cornel Schlossbauer, Munich (DE); Stephan Erbel, Munich (DE); Ulf Labsik, Aschheim (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 356 days.

(21) Appl. No.: 11/198,887

(22) Filed: Aug. 5, 2005

(65) Prior Publication Data

US 2006/0050848 A1 Mar. 9, 2006

Related U.S. Application Data

(60) Provisional application No. 60/606,176, filed on Aug. 31, 2004.

(30) Foreign Application Priority Data

Aug. 6, 2004 (EP) .................................. 04018757

(51) Int. Cl.
*A61N 5/10* (2006.01)
*A61B 6/03* (2006.01)

(52) U.S. Cl. ..................... 378/65; 378/10; 378/68; 378/69

(58) Field of Classification Search .................. 378/4, 378/10, 20, 65, 68, 69
See application file for complete search history.

(56) References Cited

U.S. PATENT DOCUMENTS 5,014,290 A * 5/1991 Moore et al. .................. 378/65
5,615,430 A 4/1997 Nambu et al.
6,148,058 A * 11/2000 Dobbs ........................ 378/10
6,269,143 B1 7/2001 Tachibana
2002/0085668 A1 7/2002 Blumhofer et al.

FOREIGN PATENT DOCUMENTS

| DE | 100 51 370 A1 | 5/2002 |
|---|---|---|
| EP | 0 562 585 A2 | 3/1993 |
| EP | 1 389 479 A1 | 2/2004 |
| WO | 01/60236 A2 | 8/2001 |

OTHER PUBLICATIONS

European Search Report for corresponding Application No. 04018757.7 dated Dec. 15, 2004.

* cited by examiner

*Primary Examiner*—Edward J. Glick
*Assistant Examiner*—Chih-Cheng G Kao
(74) *Attorney, Agent, or Firm*—Renner, Otto, Boisselle & Sklar, LLP

(57) ABSTRACT

Volumetric imaging on a radiotherapy apparatus, wherein a body, of which a volumetric image data set is to be produced, is positioned on a couch of the radiotherapy apparatus, and the couch or a bearing area of the couch or the body itself is rotated about a spatially fixed axis. During rotation, multiple x-ray images of the body or of a part of the body are produced and stored by at least one radiation source/image recorder system which is separate from the radiotherapy apparatus and whose radiation path is substantially not parallel to the spatially fixed axis. The rotational position of the couch or the bearing area of the couch or the body itself is detected while the images are produced, and the rotational position is assigned to the corresponding image, wherein a volumetric image data set of the body is reconstructed from the x-ray images by image processing and assignment by a computer system.

24 Claims, 2 Drawing Sheets

US 7,324,626 B2

VOLUMETRIC IMAGING ON A RADIOTHERAPY APPARATUS

RELATED APPLICATION DATA

This application claims priority of U.S. Provisional Application No. 60/606,176 filed on Aug. 31, 2004, which is incorporated herein by reference in its entirety.

FIELD OF THE INVENTION

The invention relates to volumetric imaging on a radiotherapy apparatus and, more specifically, to a system, method and apparatus for volumetric imaging wherein the patient is rotated to obtain the volumetric data set.

BACKGROUND OF THE INVENTION

Radiotherapy apparatus, also referred to as LINACs (linear accelerators), principally serve to administer a radiation dosage to a patient at a predetermined point on the body to treat a tumor. In such applications, it typically is desirable to take further transillumination recordings of the patient's body shortly before or during the treatment, either to check the positioning of the body or to determine any changes in treatment target area. In order to realize this, x-ray imaging is commonly employed, and in this regard DE 100 51 370 A1, for example, shows a radiotherapy and/or radiosurgery array that includes two x-ray sources. The x-ray sources are arranged above a patient couch and radiate downwards onto an image detector on the patient couch. By comparing the two-dimensional x-ray images obtained with virtual, digitally reconstructed x-ray images from previously acquired CT (computer tomograph) recordings, patient shift from a current position with respect to a desired position can be determined and the patient can be re-positioned accordingly.

Using such two-dimensional x-ray images alone allows deviations in the patient's position with regard to the translational and rotational degrees of freedom to be determined and corrected. If in addition, however, deformations within the irradiation region are to be determined on an ongoing basis, a volume data set must be produced. As a possible solution in this respect, WO 01/60236 proposes a system that includes a linear accelerator and an x-ray assembly in which the x-ray source and the image recorder are arranged transversely on a gantry and horizontal with respect to the LINAC radiation path. In this regard, the x-ray assembly and the LINAC gantry form a unit.

It is disadvantageous in principle to attach additional apparatus and therefore more weight to the LINAC gantry. The LINAC gantry rotates in a predetermined way and into predetermined positions, and additional weight impedes this rotation and makes it more difficult to maintain particular pre-sets in the rotating procedure, and therefore reduces the precision of the irradiation process. Another disadvantage of such systems is that they are only provided as a whole (i.e., as a complete unit), such that upgrading or retro-fitting other systems is not possible or extremely difficult.

SUMMARY OF THE INVENTION

The present invention enables volumetric imaging on a radiotherapy apparatus, while avoiding one or more of the aforementioned disadvantages of the prior art. In particular, the invention enables volumetric imaging that does not restrict the movement of the LINAC, and preferably enables existing systems to be adapted for volumetric imaging without major retro-fitting.

The invention further includes a method and apparatus for patient positioning on a radiotherapy apparatus, wherein an imaging method in accordance with the invention can be used. The present invention further relates to a program which, when it is running on a computer or is loaded onto a computer, causes the computer to perform a method such as described above, and to a computer program storage medium comprising such a program.

In accordance with a first aspect of the present invention, the invention includes a method for volumetric imaging on a radiotherapy apparatus. A body, of which a volumetric image data set is to be produced, is positioned on a couch of the radiotherapy apparatus. The couch or a bearing area of the couch or the body itself is rotated about a spatially fixed axis. During rotation, multiple x-ray images of the body or of a part of the body are produced and stored by at least one radiation source/image recorder system that is separate from the radiotherapy apparatus and whose radiation path is substantially not parallel to the spatially fixed axis. A rotational position of the couch or the bearing area of the couch or the body itself is detected while the images are produced, and the rotational position is assigned to the corresponding image. A computer system reconstructs a volumetric image data set of the body from the x-ray images by image processing and assignment.

In other words, an entire x-ray assembly no longer need be rotated in order to obtain a volume data set. Rather, the rotational movement required for this purpose can be generated by rotating the patient. This avoids having to modify or replace the entire gantry unit in order to obtain volumetric image data. It is sufficient to configure the patient couch or its bearing surface to rotate, which will prove simpler since such patient couches commonly include movement means. The LINAC gantry does not gain additional weight and, for this reason alone, in principle can operate more precisely and be rotated more easily. X-ray assemblies which are provided separately can often continue to be used without modifications.

In a preferred embodiment, the spatially fixed axis can pass through an isocenter of the radiotherapy apparatus, in particular perpendicular to the rotational axis of the radiotherapy apparatus and preferably vertical to the rotational axis. The rotation of the couch or the bearing area of the couch can be a continuous rotation, in particular at a constant speed. The couch preferably can be rotated about an angle of at least 180 degrees in order to obtain an optimum number of images. Rotational angle ranges which are less than and possibly substantially less than 180 degrees can of course also be considered, if suitable image processing programs are used.

In accordance with another embodiment, the x-ray images can be produced by two radiation source/image recorder systems whose radiation paths cross on the body or part of the body (containing the target region to be irradiated), wherein the radiation paths can be at an angle to each other, and the angle is preferably about 90 degrees. The volumetric data set which is reconstructed in accordance with the invention can be a reconstructed CT or MR (magnetic resonance) data set.

There also exists the possibility of detecting and tracking the rotational position of the couch or the bearing area of the couch and/or the position of the body or patient by a computer-assisted medical navigation and tracking system.

In accordance with another aspect, a patient is positioned on a couch of a radiotherapy apparatus and the position of the patient is detected and tracked by means of a computer-assisted medical navigation and tracking system. A volumetric image data set of an irradiation target region is produced by one of the aforesaid methods, and the current spatial position of the reconstructed image data set is determined. A desired position for the irradiation target region is determined in the region of the irradiating point of the radiotherapy apparatus, by the navigation system, using previously acquired patient volume image data sets, in particular CT or MR volume data sets. The deviation between the desired position and the current spatial position is ascertained. The patient and/or the irradiation target region is moved to the desired position, by relocating the couch such that a positional correction corresponds to the deviation.

Volumetric imaging can thus also be used to ensure precise patient positioning during irradiation. The data captured during volumetric imaging also can be used in other ways, for they contain current data on deformations in the irradiation target region which also can be taken into account during irradiation.

In accordance with yet another aspect, a patient is positioned on a couch of a radiotherapy apparatus and the position of the patient is detected and tracked by a computer-assisted medical navigation and tracking system. A volumetric image data set of an irradiation target region is produced by one of the aforesaid methods, and the current contour of the irradiation target or of internal organs is ascertained. The ascertained contour is compared with the contour from an irradiation plan. The treatment parameters of the radiotherapy apparatus are adapted to the newly ascertained contour of the target region.

Instead of shifting the patient, it also is possible to adapt the collimator of the radiotherapy apparatus such that the target region is hit correctly. The information on the target volume can be used not only for shifting but also to adapt or re-calculate the plan. If, for example, the prostate has become enlarged, the irradiation field is also enlarged.

Furthermore, a device for volumetric imaging on a radiotherapy apparatus includes a radiotherapy apparatus to which a couch is assigned and on which a body can be positioned, of which a volumetric image data set is to be produced. The device includes at least one radiation source/image recorder system which is separate from the radiotherapy apparatus. The radiation source/image recorder system can produce multiple x-ray images of the body or of a part of the body while the couch is rotated, wherein the radiation path of the radiation source/image recorder system is substantially not on the spatially fixed axis. The device includes a rotating device by which the couch or the bearing area of the couch or the patient is arranged such that the couch/bearing area can rotate about the spatially fixed axis. A tracking device that can detect the rotational position of the couch or the bearing area of the couch while the images are produced and the rotational position assigned to the corresponding image also is included. A computer system that stores the rotational position and image assignment and reconstructs a volumetric image data set of the body from the x-ray images by image processing and assignment.

The invention, which in this respect can comprise all the features described in this document, individually or in any combination, is explained in more detail in the following on the basis of an embodiment, wherein reference is made to the figures.

DETAILED DESCRIPTION

Figure 1:
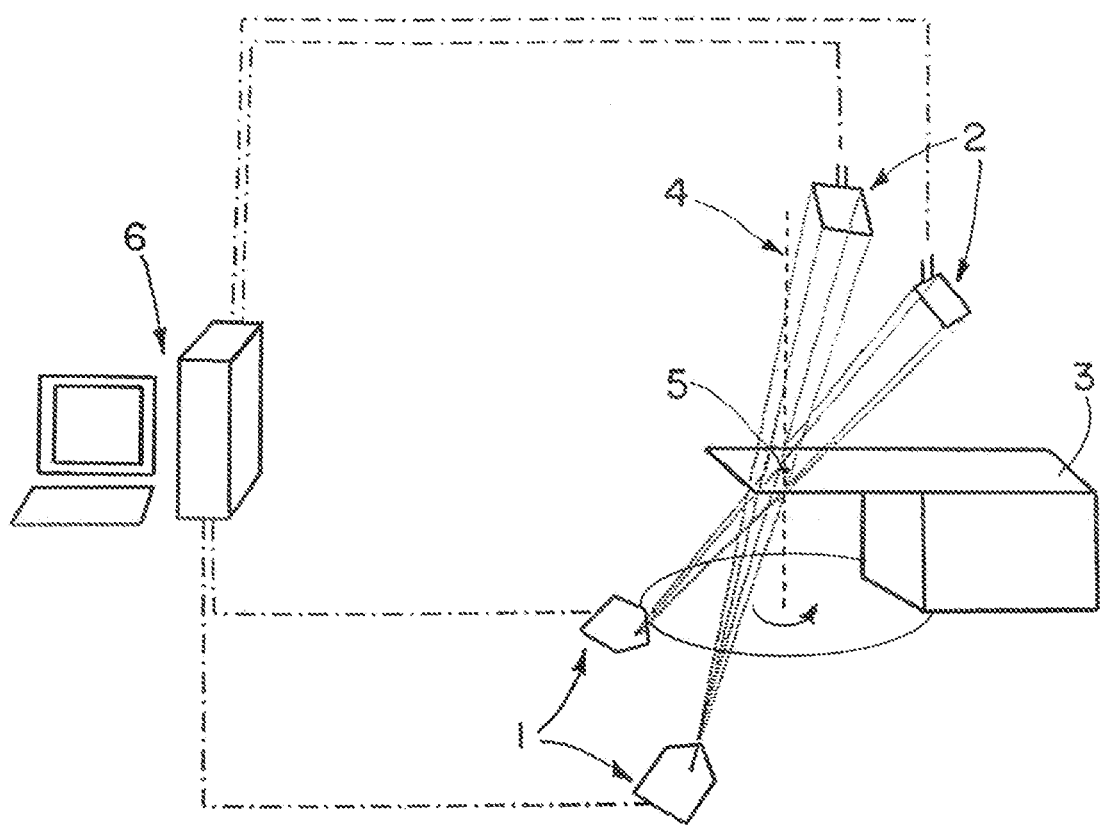
FIG. 1 schematically shows a couch that includes a couch base body on which a bearing area is arranged for the patient, and x-ray sources and detectors in relation to the couch.

With reference to FIG. 1, the isocenter of LINAC irradiation, i.e., the irradiating point which results when the LINAC gantry is rotated while irradiating, is indicated in the drawing by the reference numeral 5. The spatially fixed vertical axis 4 passes through the isocenter 5 and is the axis about which the couch 3 can rotate in order to perform the method in accordance with the invention. This can be realized, for example, by arranging the couch 3 on a rotating table on the floor. It should also be noted that the axis 4 does not necessarily have to be an isocenter axis; the axis is sufficient if it is spatially fixed and its path is known in the form of coordinates. The couch 3 stands in front of a LINAC gantry (e.g., a conventional LINAC gantry without additional x-ray image forming units) which, for the sake of clarity, is not shown.

Two x-ray tubes, each indicated by the reference numeral 1, are mounted below the patient table and the gantry (not shown) in the embodiment shown, where in the present example they are mounted in the floor. Two x-ray detectors, each bearing the reference numeral 2, are situated above the couch 3, preferably fastened to the ceiling. The detectors can be constructed in particular from amorphous silicon.

A computer system 6 is connected to the x-ray tubes 1 and the x-ray detectors 2. The computer system serves to acquire the x-ray images and to reconstruct a volume data set, for example a reconstructed CT data set, from the image information of the x-ray images.

Furthermore, a number of means can also be provided which are not shown in FIG. 1. For example, it is possible to provide a navigation or tracking system which can incorporate the task of measuring the rotational angle of the couch 3 into its conventional functions within the framework of the present invention. The rotational angle also can be ascertained directly, for example, on a rotating table using known angle-measuring devices. If, however, as is often the case, a navigation and/or tracking system is used to plan and assist in irradiating, then the navigation/tracking system can be used to determine the rotational angle for the couch 3.

Also, it is possible to provide a calibrating phantom that includes x-ray-visible markers for determining the spatial position of the x-ray system. Further, the calibration phantom can advantageously fulfill additional functions. For example, the calibration phantom can serve to define a spatial coordinate system having a point of origin in the isocenter, wherein the vertical (Z) axis of the coordinate system corresponds to the rotational axis, the Y axis defines the 0° direction of the rotational device and is perpendicular to the Z axis, and the X axis is perpendicular to the Y axis and the Z axis and defines a right-handed coordinate system (LINAC coordinate system). Additionally, the calibration phantom can serve to define the spatial position of the x-ray sources and the detectors with respect to the LINAC coordinate system, and to determine the parameters of the projective mappings of points from the LINAC coordinate system onto points in the recorded x-ray images.

In somewhat more general terms, the present invention relates in a preferred embodiment to a system for reconstructing 3D data sets from x-ray images. X-rays are shot or emitted from two fixedly installed x-ray sources 1 and x-ray images are read from x-ray detectors 2. The patient is situated on a couch 3 which can be rotated about a fixed axis 4. In order to reconstruct 3D data sets, x-ray images of the patient are produced, wherein the couch 3 is rotated further each time, from image to image. The rotational axis 4 of the couch and therefore of the patient is thus not orthogonal to the direction from an x-ray source 1 to the x-ray detector 2. The x-ray sources or tubes 1 and the x-ray detectors 2 are attached such that the beams intersect each other approximately at an angle of 90°. The two combinations of an x-ray source 1 and an x-ray detector 2 are calibrated with respect to each other. In this way, both x-ray sources 1 can be used to generate images that are used to reconstruct the CT data set. On the one hand, this accelerates the recording time for the x-ray images and on the other hand, the angular range within which x-ray images of the patient are recorded is enlarged by 90°. The rotational angle of the couch can be measured with the aid of a suitable system which, for example, can be an infrared tracking system for tracking passive markers. To this end, a suitable reference star including infrared markers is fastened to the couch.

A 3D data set is reconstructed from the recorded x-ray images with the aid of suitable computer-assisted methods. The region then to be reconstructed is preferably selected to be sufficiently large that the back projection of the CT data set onto one of the two x-ray detectors 2 from every possible couch angle covers the entire area of the detector 2.

In the following, a somewhat more detailed method sequence in which the present invention can be implemented will now be explained. The system first is calibrated, wherein the calibrating phantom is positioned in the isocenter position 5 on the couch 3 or on the bearing area of the couch 3. Two x-ray images are then recorded from the two x-ray sources 1 with the assistance of the computer system 6. Next, the projections of all the x-ray-visible markers in both x-ray images are automatically detected in the computer system 6 with the aid of image processing software. To complete calibration, the required parameters (i.e., the LINAC coordinate system, spatial position of the x-ray sources and detectors 1, 2 and parameters of the projective mappings) are calculated from the position of the phantom and the projection of the x-ray-visible markers by the computer system 6.

When actually producing and acquiring the necessary image information, the following steps are performed. The patient is positioned on the couch 3, such that the region of interest is situated around the isocenter. This image region is the region in which the irradiation target lies, e.g., a tumor.

The couch 3 then is rotated to a starting angle and the acquisition cycle begins. In the acquisition cycle, the couch 3 rotates constantly on its rotational device, about the axis 4. X-ray images are recorded such that for each recording, a particular rotational angle can be assigned to a particular point in time during a continuous recording or can be assigned to an individual x-ray image. The image data and the rotational parameters are stored in the computer system 6, and this procedure is repeated until the end angle is reached.

The subsequent operations are then completed by the computer system 6, which reconstructs a CT data set from the recorded cone-beam x-ray images with the aid of suitable computer-assisted methods (image processing).

A current volumetric image data set can therefore be easily obtained on radiotherapy apparatus with only a few modifications, wherein said data set can then also be used in accordance with another embodiment to exactly position the patient.

Figure 2:
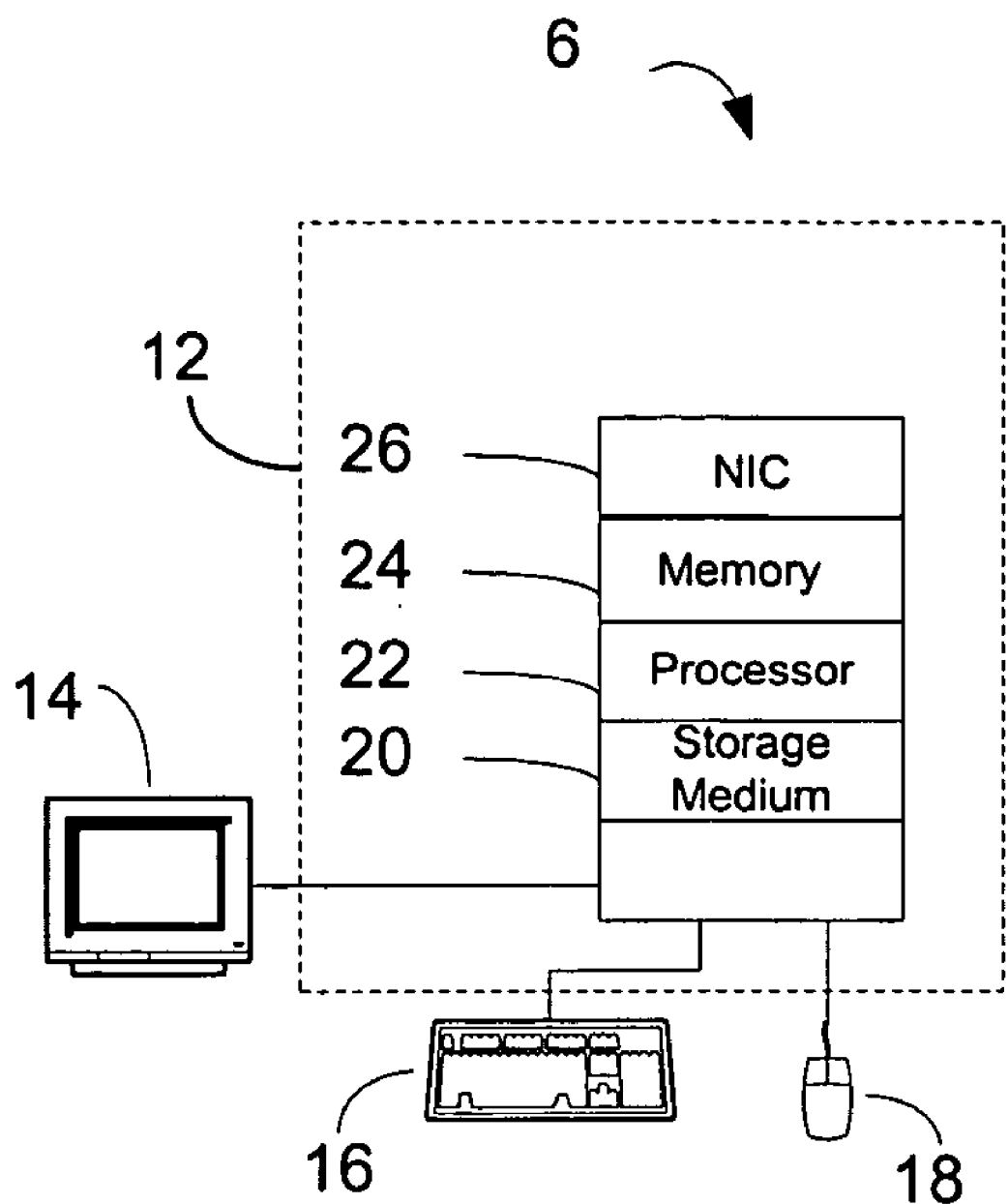
FIG. 2 is a block diagram of a computer system that can be used to implement the method of the present invention.

Moving to FIG. 2, the computer system 6 for executing a computer program in accordance with the present invention is illustrated. The computer system 6 includes a computer 12 for processing data, and a display 14 (e.g., a Cathode Ray Tube, Liquid Crystal Display, or the like) for viewing system information. A keyboard 16 and pointing device 18 may be used for data entry, data display, screen navigation, etc. The keyboard 16 and pointing device 18 may be separate from the computer 12 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 16 and pointing device 18. Touch screens may be beneficial when the available space for a keyboard 16 and/or a pointing device 18 is limited.

Included in the computer 12 is a storage medium 20 for storing information, such as application data, screen information, programs, etc. The storage medium 20 may be a hard drive, an optical drive, or the like. A processor 22, such as an AMD Athlon 64™ processor or an Intel Pentium IV® processor, combined with a memory 24 and the storage medium 20 execute programs to perform various functions, such as data entry, numerical calculations, screen display, system setup, etc. A network interface card (NIC) 26 allows the computer 12 to communicate with devices external to the computer system 6.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for volumetric imaging on a radiotherapy apparatus, comprising:
    positioning a body, of which a volumetric image data set is to be produced, on a couch of the radiotherapy apparatus;
    rotating the couch or a bearing area of the couch or the body itself about a spatially fixed axis;

during rotation, producing and storing multiple x-ray images of the body or of a part of the body by at least one radiation source/image recorder system which is separate from the radiotherapy apparatus and whose radiation path is substantially not parallel to and passes through the spatially fixed axis;

detecting the rotational position of the couch or the bearing area of the couch or the body itself while the images are produced, and assigning the rotational position to the corresponding image; and reconstructing a volumetric image data set of the body from the x-ray images by image processing and assignment by a computer system.

2. The method as set forth in claim 1, wherein the spatially fixed axis passes through an isocenter of the radiotherapy apparatus.

3. The method as set forth in claim 2, wherein the spatially fixed axis is perpendicular to the rotational axis of the radiotherapy apparatus.

4. The method as set forth in claim 2, where the spatially fixed axis is vertical as it passes through the isocenter.

5. The method as set forth in claim 1, wherein the rotation of the couch is a continuous rotation.

6. The method as set forth in claim 5, wherein the rotation of the couch is at a constant speed.

7. The method as set forth in claim 1, wherein the couch is rotated by an angle of at least 180 degrees.

8. The method as set forth in claim 1, wherein the x-ray images are produced by two radiation source/image recorder systems whose radiation paths cross on the body or part of the body, and the radiation paths are at an angle to each other.

9. The method as set forth in claim 8, wherein the angle is about 90 degrees.

10. The method as set forth in claim 1, wherein a 3D data set is reconstructed as the volumetric image data set.

11. The method as set forth in claim 1, wherein the rotational position of the couch or the bearing area of the couch and/or the position of the body or patient is detected and tracked by a computer-assisted medical navigation and tracking system.

12. A method for patient positioning on a radiotherapy apparatus, comprising:

positioning a patient on a couch of a radiotherapy apparatus, and detecting and tracking a position of the patient by a computer-assisted medical navigation and tracking system;

producing a volumetric image data set of an irradiation target region by the method as set forth in claim 1, and determining a current spatial position of the reconstructed image data set;

determining, via the navigation system, a desired position for the irradiation target region in the region of the irradiating point of the radiotherapy apparatus, the navigation system using previously acquired patient volume image data sets;

ascertaining a deviation between the desired position and the current spatial position; and moving the patient and/or the irradiation target region to the desired position by a positional correction corresponding to the deviation.

13. The method as set forth in claim 12, wherein the positional correction is obtained by relocating the couch.

14. The method as set forth in claim 12, wherein the previously acquired patient volume image data sets are CT or MR volume data sets.

15. A method for image-assisting the employment of a radiotherapy apparatus, comprising:

positioning a patient on a couch of a radiotherapy apparatus, and detecting and tracking a position of the patient by a computer-assisted medical navigation and tracking system;

producing a volumetric image data set of an irradiation target region by the method as set forth in claim 1, and ascertaining a current contour of the region irradiation target or of internal organs;

comparing the ascertained contour with a contour from an irradiation plan;

adapting treatment parameters of the radiotherapy apparatus to the ascertained contour of the target region.

16. A device for volumetric imaging on a radiotherapy apparatus, comprising:

a radiotherapy apparatus to which a couch is assigned on which a body can be positioned, wherein a volumetric image data set of the body is to be produced, said radiotherapy apparatus comprising at least one radiation source/image recorder system which is separate from the radiotherapy apparatus and by which multiple x-ray images of the body or of a part of the body are produced while the couch is rotated, wherein a radiation path of the radiation source/image recorder system is substantially not parallel to and passes through a spatially fixed axis, including:

a rotating device by which the couch or a bearing area of the couch is arranged such that the couch or bearing area rotates about the spatially fixed axis;

a tracking device configured to detect the rotational position of the couch or the bearing area of the couch while the images are produced, and assign the rotational position to the corresponding image; and a computer system configured to store the rotational position and image assignment and reconstruct a volumetric image data set of the body from the x-ray images by image processing and assignment.

17. The device as set forth in claim 16, wherein the spatially fixed axis passes through an isocenter of the radiotherapy apparatus.

18. The device as set forth in claim 17, wherein the spatially fixed axis is substantially perpendicular to the rotational axis of the radiotherapy apparatus.

19. The device as set forth in claim 17, wherein the spatially fixed axis is substantially vertical to the rotational axis of the radiotherapy apparatus.

20. The device as set forth in claim 16, comprising two radiation source/image recorder systems whose radiation paths cross on the body or part of the body at an angle with respect to each other.

21. The device as set forth in claim 20, wherein the angle is about 90 degrees.

22. The device as set forth in claim 16, wherein the computer system and the tracking device are part of a computer-assisted medical navigation and tracking system, said navigation and tracking system configured to detect or track the rotational position of the couch or the bearing area of the couch and/or the position of the body or patient.

23. A computer-readable medium encoded with a program for volumetric imaging on a radiotherapy apparatus, wherein a body of which a volumetric image data set is to be produced is positioned on a couch of the radiotherapy apparatus, wherein at least one radiation source/image recorder system is separate from the radiotherapy apparatus and whose radiation path is substantially not parallel to and passes through a spatially fixed axis, the program comprising:
- code that directs a rotation of the couch or a bearing area of the couch or the body itself about the spatially fixed axis;
- code that during said rotation directs the radiation source/image recorder system to acquire multiple x-ray images of the body or of a part of the body;
- code that detects the rotational position of the couch or bearing area of the couch or the body itself while the images are produced;
- code that assigns the rotational position to the corresponding image; and
- code that reconstructs a volumetric image data set of the body from the x-ray images by image processing and assignment by a computer system.

24. A system for volumetric imaging on a radiotherapy apparatus, wherein a body of which a volumetric image data set is to be produced is positioned on a couch of the radiotherapy apparatus, wherein at least one radiation source/image recorder system is separate from the radiotherapy apparatus and whose radaiation path is substantially not parallel to and passes through a spatially fixed axis, comprising:
- a processor circuit having a processor and a memory;
- a volumetric imaging subsystem stored in the memory and executable by the processor, the subsystem comprising:
- logic that directs a rotation of the couch or a bearing area of the couch or the body itself about the spatially fixed axis;
- logic that during said rotation directs the radiation source/image recorder system to acquire multiple x-ray images of the body or of a part of the body;
- logic that detects the rotational position of the couch or the bearing area of the couch or the body itself while the images are produced;
- logic that assigns the rotational position to the corresponding image; and
- logic that reconstructs a volumetric image data set of the body from the x-ray images by image processing and assignment by a computer system.

* * * * *